United States Patent [19]

Alt et al.

[11] Patent Number: 5,627,247
[45] Date of Patent: *May 6, 1997

[54] ORGANOMETALLIC FLUORENYL COMPOUNDS AND USE THEREOF IN OLEFIN POLYMERIZATION

[75] Inventors: Helmut G. Alt, Bayreuth, Germany; Gil R. Hawley, Dewey, Okla.; Paul D. Smith, Seabrook, Tex.; Syriac J. Palackal, Bartlesville, Okla.; Michael Schmid, Bayreuth, Germany; M. Bruce Welch, Bartlesville, Okla.; Konstantinos Patsidis, Berlin, Germany; Rolf L. Geerts, Bartlesville, Okla.; Eric T. Hsieh, Bartlesville, Okla.; Max P. McDaniel, Bartlesville, Okla.

[73] Assignee: Phillips Petroleum Company, Bartlesville, Okla.

[ * ] Notice: The term of this patent shall not extend beyond the expiration date of Pat. No. 5,436,305.

[21] Appl. No.: 408,468

[22] Filed: Mar. 22, 1995

Related U.S. Application Data

[63] Continuation-in-part of Ser. No. 194,944, Feb. 14, 1994, abandoned, and a continuation of Ser. No. 226,600, Apr. 12, 1994, abandoned, which is a continuation-in-part of Ser. No. 192,223, Feb. 3, 1994, which is a continuation of Ser. No. 734,853, Jul. 23, 1991, Pat. No. 5,436,305, which is a continuation-in-part of Ser. No. 697,363, May 9, 1991, Pat. No. 5,191,132, said Ser. No. 194,944, Feb. 14, 1994, abandoned, is a continuation-in-part of Ser. No. 71,906, Jun. 3, 1993, abandoned.

[51] Int. Cl.$^6$ .................... C08F 4/642; C08F 10/04; C07F 17/00
[52] U.S. Cl. .............. 526/160; 526/351; 526/352; 526/943; 502/103; 502/117; 502/152; 556/43; 556/52; 556/53; 556/58
[58] Field of Search ................ 556/52, 43, 53, 556/58; 502/152, 103, 117; 526/160, 170, 943, 351, 352

[56] References Cited

U.S. PATENT DOCUMENTS

| 5,120,867 | 6/1992 | Welborn, Jr. | 556/12 |
|---|---|---|---|
| 5,124,418 | 6/1992 | Welborn, Jr. | 526/114 |
| 5,225,501 | 7/1993 | Fujita et al. | 526/127 |
| 5,304,523 | 4/1994 | Razavi | 526/170 X |
| 5,436,305 | 7/1995 | Alt et al. | 526/170 X |

*Primary Examiner*—Fred Teskin
*Attorney, Agent, or Firm*—Edward L. Bowman

[57] ABSTRACT

Unbridged fluorenyl containing metallocenes are disclosed along with methods for making the metallocenes. Also disclosed are methods for using the metallocenes as polymerization catalysts. In addition, polymers resulting from such polymerizations are disclosed.

48 Claims, No Drawings

ORGANOMETALLIC FLUORENYL COMPOUNDS AND USE THEREOF IN OLEFIN POLYMERIZATION

This application of U.S. patent application Ser. No. 08/226,600 filed Apr. 12, 1994 now abandoned, which is continuation-in-part of U.S. patent application Ser. No. 08/192,223 filed Feb. 3, 1994, which was a continuation of U.S. patent application Ser. No. 07/734,853 filed Jul. 23, 1991, now U.S. Pat. No. 5,436,305, which was a continuation-in-part of U.S. patent application Ser. No. 697,363 filed May 9, 1991, now U.S. Pat. No. 5,191,132. The disclosure of all those applications are incorporated herein by reference. This application is also a continuation-in-part of U.S. patent application Ser. No. 194,944, filed Feb. 14, 1994, now abandoned, which was a continuation-in-part of U.S. patent application Ser. No. 71,906 filed Jun. 3, 1993, now abandoned.

This invention relates to organometallic compounds. More specifically, this invention relates to organometallic compounds containing at least one fluorenyl ligand. In another aspect, this invention relates to polymerization catalyst systems which contain organometallic fluorenyl compounds. In still another aspect, this invention relates to a method for polymerizing olefins using such organometallic fluorenyl compounds and to the polymers resulting from such polymerizations.

BACKGROUND OF THE INVENTION

Since the discovery of ferrocene in 1951, a number of metallocenes have been prepared by the combination of compounds having the cyclopentadienyl structure with various transition metals. The term "cyclopentadienyl structure" as used herein refers to the following structure.

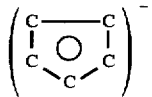

The term "cyclopentadiene-type compounds" as used herein refers to compounds containing the cyclopentadiene structure. Examples include unsubstituted cyclopentadiene, unsubstituted indene, unsubstituted fluorene, and substituted varieties of such compounds. Also included is tetrahydro indene.

Many of the cyclopentadiene-type metallocenes have been found useful in catalyst systems for the polymerization of olefins. It has been noted in the art that variations in the chemical structure of such cyclopentadienyl-type metallocenes can have significant effects upon the suitability of the metallocene as a polymerization catalyst. For example, the size and substitutions on cyclopentadienyl-type ligands has been found to affect the activity of the catalyst, the stereoselectivity of the catalyst, the stability of the catalyst, and other properties of the resulting polymer; however, the effects of various substituents is still largely an empirical matter, that is, experiments must be conducted in order to determine just what effect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

While there are references in the prior art which have envisioned metallocenes containing fluorenyl groups, only a very limited number of fluorenyl-containing metallocenes have actually been prepared prior to the present invention. The Journal of Organometallic Chemistry, Vol. 113, pages 331-339 (1976), the disclosure of which is incorporated herein by reference, discloses preparing bis-fluorenyl zirconium dichloride and bis-fluorenyl zirconium dimethyl. U.S. Pat. No. 4,892,851 and the New Journal of Chemistry, Vol. 14, pages 499-503, dated 1990, the disclosures of which are incorporated herein by reference, each disclose preparing a metallocene from the ligand 1,1-dimethylmethylene-1-(fluorenyl)-1-(cyclopentadienyl). The New Journal of Chemistry article also discloses preparing a similar compound in which the cyclopentadienyl group has a methyl substituent in the number 3 position.

An object of the present invention is to provide certain new fluorenyl-containing metallocenes. Another object of the present invention is to provide a method for preparing new fluorenyl-type metallocenes. Still another object of the present invention is to provide polymerization catalysts employing fluorenyl-type metallocenes. Still yet another object of the present invention is to provide processes for the polymerization of olefins using fluorenyl-type metallocene catalyst systems. Still yet another object of the present invention is to provide polymers produced using such fluorenyl-containing metallocene catalysts.

SUMMARY OF THE INVENTION

In accordance with the present invention, there are provided new metallocenes of the formula $(FlR_n)(CpR_m)_p MeQ_k$ wherein Fl is a fluorenyl radical; Cp is a cyclopentadienyl, indenyl, or tetrahydroindenyl radical; each R is the same or different and is a halide or an organo radical having 1 to 20 carbon atoms; Me is metal selected from the group consisting of IVB, VB, and VIB metals of the Periodic Table; each Q is the same or different and is selected from the group consisting of hydrocarbyl or hydrocarbyloxy radicals having 1 to 20 carbon atoms, hydrogen, and halogens; p is 1 or 2; is a number sufficient to fill out the remaining valences of Me; n is a number in the range of 0 to 8; m is a number in the range of 0 to 7, further characterized by the fact that Fl has no R in the 9 position.

In accordance with another aspect of the present invention, there is provided a method for forming fluorenyl-containing metallocenes comprising reacting an alkali metal salt of the selected fluorenyl compound with a transition metal compound of the formula $(CpR_m)_p MeQ_k$, wherein p and k are as defined above, in the presence of a non-halogenated solvent for the fluorenyl salt which solvent is non-coordinating with the transition metal halide.

In accordance with still another aspect of the present invention, there is provided a process for the polymerization of olefins comprising contacting said olefins under suitable reaction conditions with a catalyst system comprising a fluorenyl-containing metallocene as described above in combination with a suitable co-catalyst.

Still further in accordance with the present invention there is provided the polymer products resulting from such polymerizations.

DETAILED DESCRIPTION OF THE INVENTION

The novel metallocenes provided in accordance with the present invention are unbridged, that is the fluorenyl ligand and the other cyclopentadienyl-type ligands that are bound to the metal are not bound to each other. These metallocenes are referred to as unbridged metallocenes regardless of whether the bonding between the metal and the cyclopentadienyl-type components is sigma or pi bonding, or pentahapto, trihapto, or monohapto.

Methods for preparing fluorenyl-containing compounds which can be used in making the metallocenes are disclosed in the aforementioned U.S. patent applications Ser. Nos. 697,363 and 192,223.

The metal, Me is selected from the group IV, VB, or VIB metals of the Periodic Table. The currently preferred metals include zirconium, and hafnium.

The substituents R can be selected from a wide range of organo substituents. In the preferred embodiments the substituents R are each independently selected from hydrocarbyl or hydrocarbyloxy radicals having 1 to 20 carbon atoms. In a particularly preferred embodiment, the radicals R are alkyl radicals. More preferably the alkyl R radicals have 1 to 5 carbon atoms.

Each Q is a hydrocarbyl radical such as, for example, aryl, alkyl, alkenyl, alkaryl, or arylalkyl radical having from 1 to 20 carbon atoms, hydrocarbyloxy radicals having 1 to 20 carbon atoms, hydrogen, or halogen. Exemplary Q hydrocarbyl radicals include methyl, ethyl, propyl, butyl, amyl, isoamyl, hexyl, isobutyl, heptyl, octyl, nonyl, decyl, cetyl, 2-ethylhexyl, phenyl, fluorenyl, and the like. Exemplary halogen atoms include chlorine, bromine, fluorine, and iodine and of these halogen atoms, chlorine is currently preferred. Exemplary hydrocarboxy radicals include methoxy, ethoxy, propoxy, butoxy, amyloxy, phenyloxy, and the like.

Illustrative, but non-limiting examples of unbridged metallocenes falling within the scope of the above formula include (fluorenyl) (cyclopentadienyl) zirconium dichloride, (2,7-dimethyl fluorenyl) (cyclopentadienyl) zirconium dichloride, (2,7-diethyl fluorenyl) (cyclopentadienyl) zirconium dichloride, (2,7-di-t-butyl fluorenyl) (cyclopentadienyl) zirconium dichloride, (2,7-dimethoxy fluorenyl) (cyclopentadienyl) zirconium dichloride, (4-methyl-5-methyl fluorenyl) (cyclopentadienyl) zirconium dichloride, (2,7-dimesityl fluorenyl) (cyclopentadienyl) zirconium dichloride, (2,7-di(alpha-methyl vinyl) fluorenyl) (cyclopentadienyl) zirconium dichloride, (2,7 dibromo fluorenyl) (cyclopentadienyl) zirconium dichloride, (1-methyl fluorenyl) (cyclopentadienyl) zirconium dichloride, (2-t-butyl fluorenyl) (cyclopentadienyl) zirconium dichloride, (2-ethyl fluorenyl) (cyclopentadienyl) zirconium dichloride, (2-bromo fluorenyl) (cyclopentadienyl) zirconium dichloride, (4-methyl fluorenyl) (cyclopentadienyl) zirconium dichloride, (fluorenyl) (cyclopentadienyl) titanium dichloride, (fluorenyl) (pentamethylcyclopentadienyl) zirconium dichloride, (fluorenyl) (pentamethylcyclopentadienyl) hafnium dichloride, (2,7-dimethyl fluorenyl) (pentamethylcyclopentadienyl) hafnium dichloride, (2,7-dimethylfluorenyl) (pentamethylcyclopentadienyl) zirconium dichloride, (2,7-di-t-butylfluorenyl) (pentamethylcyclopentadienyl) hafnium dichloride, (4-(cyclopentadienylmethyl) fluorenyl) (cyclopentadienyl) zirconium dichloride, (2,7-di(t-butyl)-4-(cyclopentadienyl methyl) fluorenyl) (cyclopentadienyl) zirconium dichloride, (2,7-di-t-butylfluorenyl) (pentamethylcyclopentadienyl) zirconium dichloride, (2,7-diethylfluorenyl) (pentamethylcyclopentadienyl) zirconium dichloride, (4,5-dimethylfluorenyl) (pentamethylcyclopentadienyl) zirconium dichloride, (2-t-butylfluorenyl) (pentamethylcyclopentadienyl) zirconium dichloride, (fluorenyl) bis(3-methylcyclopentadienyl) zirconium chloride, (2,7 di-t-butyl fluorenyl) bis(3-methylcyclopentadienyl) zirconium chloride, bis(fluorenyl) bis(cyclopentadienyl) zirconium, and the like.

Particularly preferred metallocene species include unbridged metallocenes containing at least one substituted fluorenyl radical, i.e., there is at least one FlRn wherein n is 1 to 8.

The inventive metallocenes as well as related metallocenes can be prepared by reacting an alkali metal salt of the fluorenyl compound with a suitable transition metal compound in a suitable solvent under suitable reaction conditions.

The term transition metal compound as used herein includes compounds of the formula MeQk wherein Me, Q, and k are as defined above. Some non-limiting examples include zirconium tetrachloride, hafnium tetrachloride, cyclopentadienyl zirconium trichloride, fluorenyl zirconium trichloride, 3-methylcyclopentadienyl zirconium trichloride, indenyl zirconium trichloride, 4-methyl fluorenyl zirconium trichloride, bis (3-methylcyclopentadienyl) zirconium dichloride, bis (cyclopentadienyl) zirconium dichloride and the like.

The currently preferred unbridged metallocenes are prepared by reacting a substituted fluorenyl alkali metal salt with an inorganic or cyclopentadienyl-type halide compound of the Group IVB, V B, VIB metals, especially zirconium and hafnium.

Metallocenes in which Q is a hydrocarbyl or hydrocarbyloxy can be readily prepared by reacting the halide form of the metallocene with an alkali metal salt of the hydrocarbyl or hydrocarbyloxy radical under conditions as have been used in the past for forming such ligands in prior art metallocenes. See, for example, the aforemention J. Org. Chem. 113, 331–339 (1976). Another approach involves reacting a compound of the formula MeQk wherein at least one Q is hydrocarbyl or hydrocarbyloxy with the alkali metal salt of the fluorenyl compound.

One embodiment of the present invention involves carrying out the reaction of the fluorenyl-containing salt and the transition metal compound in the presence of a liquid diluent which is non-halogenated and non-coordinating toward the transition metal compound. Examples of such suitable liquid include hydrocarbons such as toluene, pentane, or hexane as well as non-cyclic ether compounds such as diethylether. It has been found that the use of such non-halogenated non-coordinating solvents generally allows one to obtain large amounts of substantially pure metallocenes in a more stable form, and often allows the reaction to be conducted under higher temperature conditions, than when dichloromethane is used as the diluent. In an especially preferred embodiment, the fluorenyl-containing salt, used to form the ligand, is also prepared in a liquid diluent that is non-halogenated and non-coordinating toward the transition metal.

The formation of the alkali metal salt of the fluorenyl compound can be formed using generally any technique known in the art. For example, such can be prepared by reacting an alkali metal alkyl with the cyclopentadienyl-type compound. The molar ratio of the alkali metal alkyl to the fluorenyl cyclopentadienyl-type compound present can vary; generally however, the ratio would be in the range of about 0.5/1 to about 1.5/1, still more preferably about 1/1.

Typically, the alkali metal of the alkali metal alkyl would be selected from sodium, potassium, and lithium, and the alkyl group would have 1 to 8 carbon atoms, more preferably 1 to 4 carbon atoms. Preferably if the fluorenyl salt is formed using tetrahydrofuran (THF) as the liquid solvent, the salt is isolated and substantially all of the THF is removed before the salt is contacted with the transition metal halide. The molar ratio of the fluorenyl compound to the transition metal compound can vary over a wide range depending upon the results desired. Typically, however, the fluorenyl compound is used at a molar ratio of the fluorenyl compound to the transition metal compound of about 1 to 1.

The resulting metallocene can be recovered and purified using conventional techniques known in the art such as filtration, extraction, crystallization, and re-crystallization. It is generally desirable to recover the metallocene in a form that is free of any substantial amount of by-product impurities. Accordingly, recrystallization and fractional crystallization to obtain relatively pure metallocenes is desireable. Dichloromethane has been found to be particularly useful for such recrystallizations. Since the stability of the various metallocenes varies, it is generally desirable to use the metallocenes soon after their preparation or at least to store the metallocene under conditions favoring their stability. For example the metallocenes can generally be stored in the dark at low temperature, i.e. below 0° C. in the absence of oxygen or water.

The resulting fluorenyl containing metallocenes can be used in combination with a suitable co-catalyst for the polymerization of olefinic monomers. In such processes the metallocene or the co-catalyst can be employed on a solid insoluble particulate support.

Examples of suitable co-catalysts include generally any of those organometallic co-catalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethyl aluminum, tri-isobutyl aluminum, diethyl aluminum chloride, diethyl aluminum hydride, and the like.

The currently most preferred co-catalyst is an aluminoxane. Such compounds include those compounds having repeating units of the formula

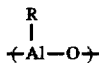

where R is an alkyl group generally having 1 to 5 carbon atoms. Aluminoxanes, also sometimes referred to as poly (hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methyl aluminum oxide) and poly(ethyl aluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with the aluminoxane co-catalyst can be used to polymerize olefins. Generally such polymerizations would be carried out in a homogeneous system in which the catalyst and co-catalyst were soluble; however, it is within the scope of the present invention to carry out the polymerizations in the presence of supported forms of the catalyst and/or co-catalyst in a slurry or gas phase polymerization. It is within the scope of the invention to use a mixture of two or more fluorenyl-containing metallocenes or a mixture of an inventive fluorenyl-containing metallocene with one or more other cyclopentadienyl-type metallocenes.

The fluorenyl-containing metallocenes when used with aluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-methylpentene-1, heptene-1, octene-1, decene-1, 4,4-dimethyl-1-pentene, 4,4-diethyl-1-hexene, 3-4-dimethyl-1-hexene, and the like and mixtures thereof. The catalysts are particularly useful for preparing copolymers of ethylene or propylene and generally a minor amount, i.e. no more than about 20 mole percent, more typically less than about 10 mole percent, of the higher molecular weight olefin.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

Generally the molar ratio of the aluminum in the aluminoxane to the transition metal in the metallocene would be in the range of about 0.1:1 to about $10^5:1$ and more preferably about 5:1 to about $10^4:1$. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperatures typically would be in the range of about −60° C., to about 280° C., more preferably in the range of about 20° C. to about 160° C. Typically the pressure would be in the range of from about 1 to about 500 atmospheres or greater.

The polymers produced with this invention have a wide range of uses that will be apparent to those skilled in the art from the physical properties of the respective polymer.

A further understanding of the present invention, its various aspects, objects and advantages will be provided by the following examples.

In the following examples, the metallocene preparations were carried out routinely using the Schlenk technique, with strict exclusion of air and moisture, by means of purified and dried inert gas.

The solvents which were used were dried over a sodium/potassium alloy or over phosphorus pentoxide in the case of dichloromethane and distilled in circulation equipment under an inert atmosphere. Toluene was additionally distilled over phosphorus pentoxide and dichloromethane was distilled over calcium hydride. Deuterated solvents for the NMR spectroscopy were stored over a molecular sieve.

The melting points of the organic compounds were determined in open tubes and those of the organometallic compounds were determined in closed tubes under nitrogen.

The organic compounds were characterized using a gas chromatograph with flame ionization detector and a fused silica column with helium as the carrier gas. The mass spectra was carried out using a mass spectrometer with electron impact ionization energy of 70 eV. The samples were introduced with the help of a direct inlet system or they were injected in the form of solutions.

Crystal structure investigations were conducted using a Mo-K alpha radiation ($\gamma$=0.71073 Å) using a defractometer.

EXAMPLES

Example I

About 2.4 mmol of fluorene was dissolved in 50 ml of ether and mixed with 1.5 ml of a 1.6 molar hexane solution of butyllithium at room temperature. After termination of the evolution of gas, an equal molar quantity of cyclopentadienyl zirconium trichloride was added and the mixture stirred for one hour. The solvent was then removed using the vacuum from a membrane pump. The remaining residue was extracted with toluene and filtered over sodium sulfate. The filtrate was concentrated by evaporation and brought to the point of crystallization. The resulting bright orange solid product was determined to be (fluorenyl) (cyclopentadienyl) zirconium dichloride, hereinafter referred to as Catalyst No. 27. $^1$H-NMR, $^{13}$C-NMR spectroscopy, mass spectrometer and decomposite temperatures were used to identify the compound. The mass spectrum indicated a molecular weight of 392. The material decomposed at 167° C. The $^1$H-NMR spectra showed a singlet resonance at about 6.08 which can be assigned to the protons of the $C_5H_5$ ring and multiplet resonances in the regions of about 7.38–7.48 and about 7.57. A doublet was observed at about 8.13 and there was resonance at about 6.53.

It should be noted that the $^1$H-NMR spectrum, melting point, and color of this product did not correspond to what was reported by Scharma and Kaushik for the product which they named (cyclopentadienyl) (fluorenyl) zirconium dichloride which they prepared by reacting fluorenyl thallium with cyclopentadienyl zirconium trichloride in THF. (Acta Chim. Hung., 116, 361 (1984))

Example II

Using the same general technique as set forth in Example I, a number of additional metallocenes were prepared using different substituted fluorenyl ligands. Those reactions resulted in the following catalysts.

| Catalyst No. | Name |
|---|---|
| 28 | (2,7 dimethylfluorenyl)(cyclopentadienyl)ZrCl$_2$ |
| 29 | (2,7 diethylfluorenyl)(cyclopentadienyl)ZrCl$_2$ |
| 30 | (2,7 di-t-butylfluorenyl)(cyclopentadienyl)ZrCl$_2$ |
| 31 | (2,7 dimethoxyfluorenyl)(cyclopentadienyl)ZrCl$_2$ |
| 32 | (2,7 dibromofluorenyl)(cyclopentadienyl)ZrCl$_2$ |
| 33 | (2,7 di-α-methylvinylfluorenyl)(cyclopentadienyl)ZrCl$_2$ |
| 34 | (2,7 dimesitylfluorenyl)(cyclopentadienyl)ZrCl$_2$ |
| 35 | (4,5 dimethylfluorenyl)(cyclopentedienyl)ZrCl$_2$ |
| 36 | (1-methylfluorenyl)(cyclopentadienyl)ZrCl$_2$ |
| 37 | (2-methylfluorenyl)(cyclopentadienyl)ZrCl$_2$ |
| 38 | (2-ethylfluorenyl)(cyclopentadienyl)ZrCl$_2$ |
| 39 | (2-t-butylfluorenyl)(cyclopentadienyl)ZrCl$_2$ |
| 40 | (2-bromofluorenyl)(cyclopentadienyl)ZrCl$_2$ |
| 41 | (4-methylfluorenyl)(cyclopentadienyl)ZrCl$_2$ |

Example III

About 2.4 mmol of fluorene was dissolved in 50 ml of diether and mixed with 1.5 ml of a 1.6M hexane solution of butyllithium at room temperature. After termination of the evolution of the gas, an equal molar quantity of cyclopentadienyl zirconium trichloride was added. After a reaction time of one hour, the mixture was mixed with 3 ml (4.8 mmol) of a 1.6M diethylether solution of methyllithium and stirred for a further 30 min. The solvent was removed in a vacuum. The residue was taken up in pentane and the mixture filtered over sodium sulfate. After concentrating the solution by evaporation and crystallization, a solid product is obtained. The solid product has been identified as (cyclopentadienyl)(fluorenyl) zirconium dimethyl, hereinafter referred to as Catalyst No. 52. This same product can be produced by reacting Catalyst No. 27 with two equivalents of the methyllithium.

Using one or the other of these two methods, several additional dimethyl zirconium metallocenes were produced, namely:

| Catalyst No. | Name |
|---|---|
| 53 | (2,7-dimethylfluorenyl)(cyclopentadienyl)(dimethyl)Zr |
| 54 | (2,7-diethylfluorenyl)(cyclopentadienyl)(dimethyl)Zr |
| 55 | (2,7-dibromofluorenyl)(cyclopentadienyl)(dimethyl)Zr |
| 56 | (4,5-dimethylfluorenyl)(cyclopentadienyl)(dimethyl)Zr |
| 57 | (2-methylfluorenyl)(cyclopentadienyl)(dimethyl)Zr |
| 58 | (2-ethylfluorenyl)(cyclopentadienyl)(dimethyl)Zr |

Example IV

A solution of 0.53 g of fluorene in 50 ml of diethyl ether was mixed at room temperature with 2 ml of a 1.6M hexane solution of butyllithium. After the termination of the evolution of gas, 0.47 g of bis(cyclopentadienyl) zirconium dichloride was added and the mixture stirred for an additional 30 min to result in an orange suspension. The mixture was then extracted with diethyl ether and the solution filtered over sodium sulfate. The filtrate was concentrated by evaporation and brought to the point of crystallization. The product bis(cyclopentadienyl) bis(fluorenyl) zirconium, was recovered. That metallocene will be referred to hereinafter as Catalyst No. 78.

Example V

About 2.4 mmol of fluorene was dissolved in 50 ml of diethylether and mixed with 1.5 ml of a 1.6M hexane solution of butyllithium and stirred for 2 hrs at room temperature. Then 0.77 g of bis(methylcyclopentadienyl) zirconium dichloride was added. The reaction mixture was then stirred for an addition 90 mins. Then the solvent was removed using a vacuum. The residue was extracted with toluene and a suspension filtered over sodium sulfate. The filtrate was freed from solvent and taken up in 50 ml of diethylether. Crystallization at −30° C. yields the product bis(methylcyclopentadienyl) (fluorenyl) zirconium chloride, referred to hereinafter as Catalyst No. 79. The x-ray analysis of the solid Catalyst No. 79 is believed to demonstrate that the fluorenyl is a σ-bound ligand rather than a π-bound ligand.

Using a similar method but starting with 2,7 dimethylfluorene rather than fluorene, the product bis (methylcyclopentadienyl) (2,7-dimethylfluorenyl) zirconium chloride was obtained. This catalyst will be referred to hereinafter as Catalyst No. 80.

Example VI

A process like that used in Example I was repeated by substituting either pentamethylcyclopentadienyl zirconium trichloride or pentamethylcyclopentadienyl hafnium trichloride for the cyclopentadienyl zirconium trichloride. This resulted in the following catalysts:

| Catalyst No. | Name |
|---|---|
| 63 | (fluorenyl)(pentamethylcyclopentadienyl) ZrCl$_2$ |
| 64 | (fluorenyl)(pentamethylcyclopentadienyl) HfCl$_2$ |
| 65 | (2,7 dimethylfluorenyl)(pentamethylcyclopentadienyl) ZrCl$_2$ |
| 66 | (2,7 dimethylfluorenyl)(pentamethylcyclopentadienyl) HFCl$_2$ |
| 67 | (2,7 di-t-butylfluorenyl)(pentamethylcyclopentadienyl) ZrCl$_2$ |
| 68 | (2,7 di-t-butylfluorenyl)(pentamethylcyclopentadienyl) HfCl$_2$ |
| 69 | (2,7 diethylfluorenyl)(pentamethylcyclopentadienyl) ZrCl$_2$ |
| 70 | (4,5 dimethylfluorenyl)(pentamethylcyclopentadienyl) ZrCl$_2$ |
| 71 | (2-t-butylfluorenyl)(pentamethylpentadienyl) ZrCl$_2$ |

Example VII

Ethylene Polymerization

A number of the metallocenes prepared in the above examples were evaluated for the polymerization of ethylene. In each case, the metallocene was activated by dissolving in toluene and then mixing with a 30 Molar % toluene solution of methylaluminoxane. The formation of the active catalyst system solution expressed itself by a change in color.

The polymerizations were conducted by introducing 500 ml of pentane into a 1 liter autoclave with an internal temperature of 10° C. Then 5 ml of the catalyst system solution was introduced. After this, an ethylene pressure of 10 bar was applied and the reaction mixture was stirred for 1 hr at 10° C. The polymer which was obtained was filtered off and subsequently washed in each case with 300 ml of dilute caustic soda solution, water, and then acetone, and liberated from the residual solvent by drying in a cabinet at 130° C. The results of the polymerizations with the various metallocenes is summarized in Table I.

TABLE I

| Catalyst | Amount [mg] | Polyethylene [g] | Activity [kg PE / g Metal-hr] |
|---|---|---|---|
| Cp$_2$ZrCl$_2$ | 2.0 | 40 | 64 |
| 27 | 2.0 | 80 | 172 |
| 28 | 1.5 | 70 | 219 |
| 30 | 1.5 | 60 | 221 |
| 31 | 1.9 | 16 | 44 |
| 32 | 1.5 | 13 | 53 |
| 33 | 1.5 | 50 | 172 |
| 34 | 2.0 | 93 | 318 |
| 35 | 1.9 | 83 | 200 |
| 36 | 1.4 | 93 | 301 |
| 37 | 2.0 | 70 | 159 |
| 39 | 1.9 | 65 | 170 |
| 40 | 1.5 | 25 | 86 |
| 41 | 2.2 | 76 | 153 |
| 63 | 2.1 | 55 | 137 |
| 64 | 2.4 | 44 | 39 |
| 65 | 1.5 | 60 | 190 |
| 66 | 2.0 | 14 | 22 |
| 67 | 1.7 | 50 | 183 |
| 68 | 2.4 | 22 | 34 |
| 70 | 2.5 | 40 | 88 |
| 71 | 1.9 | 59 | 175 |
| 76 | 2.0 | 2 | 11 |
| 78 | 1.9 | 14 | 44 |
| 79 | 1.9 | 43 | 112 |

The catalysts having two hydrocarbyl sustitutents on the fluorenyl (i.e. Catalysts 28, 30,33-36) appear to be somewhat more active than those having only one hydrocarbyl substituent on the fluorenyl (i.e. Catalysts (37,39, 41). Electron withdrawing substituents appear to reduce the activity. See catalysts 31, 32, and 41. Replacing cyclopentadienyl with pentamethylcyclopentadienyl appears to reduce activity at least under these polymerization conditions. Compare Catalysts 63, 65, 67, and 70 with 17, 18, 30, and 35 respectively. Of particular note is the fact that generally the introduction of a fluorenyl radical results in a more active catalyst. Compare for example the control catalyst biscyclopentadienyl zirconium dichloride with Catalyst 27.

Example VIII

Propylene Polymerization

The unbridged metallocene Catalyst Nos. 27, 28, and 65 were evaluated for the polymerization of propylene. The polymerizations were carried out in the same type of autoclave used for the ethylene polymerizations. For the purpose of drying 500 ml of liquid propylene was mixed with 10 ml of the aforementioned toluene solution of methylaluminoxane and stirred for 30 minutes at 20 degrees C. Once the autoclave had cooled down to −10 degrees C., the catalyst solution, i.e. metallocene and methylaluminoxane as prepared for the ethylene polymerizations, was added to the autoclave. The autoclave was then heated up to 60 degrees C. and held at that temperature for one hour. In all cases the recovered polymer was a tacky material appearing to be substantially atactic polypropylene.

That which is claimed is:

1. An unbridged metallocene of the formula (FlR$_n$)(CpR$_m$)MeQ$_k$ wherein Fl is a fluorenyl radical, Cp is a cyclopentadienyl or indenyl radical, each R is the same or different and is an organo radical having 1 to 20 carbon atoms, Me is a metal selected from the group consisting of IVB metals of the Periodic Table, each Q is the same or different and is selected from the group consisting of hydrocarbyl or hydrocarbyloxy radicals having 1 to 20 carbon atoms and halogens, k is a number sufficient to fill out the remaining valences of Me, n is a number in the range of 0 to 7, m is a number in the range of 0 to 7, further characterized by the fact that the Fl has no R in the 9 position.

2. A metallocene according to claim 1 wherein each Q is the same and is selected from the group consisting of halides and alkyl radicals having one to five carbon atoms.

3. A metallocene according to claim 2 wherein Cp is cyclopentadienyl.

4. A metallocene according to claim 3 wherein m is 0.

5. A metallocene according to claim 4 wherein n is a number in the range of 1 to 4.

6. A metallocene according to claim 3 wherein m is a number in the range of 1 to 5.

7. A metallocene according to claim 6 wherein Me is selected from Zr and Hf.

8. A metallocene according to claim 1 wherein Me is selected from Zr and Hf.

9. A metallocene according to claim 8 wherein Cp is cyclopentadienyl.

10. A metallocene according to claim 9 wherein m is 1 to 5.

11. A metallocene according to claim 1 selected from the group consisting of:

(fluorenyl)(cyclopentadienyl) zirconium dichloride, (2,7-dimethyl fluorenyl) (cyclopentadienyl) zirconium dichloride, (2,7-diethyl fluorenyl) (cyclopentadienyl) zirconium dichloride, (2,7-di-t-butyl fluorenyl) (cyclopentadienyl) zirconium dichloride, (2,7-dimethoxy fluorenyl) (cyclopentadienyl) zirconium dichloride, (4-methyl-5-methyl fluorenyl) (cyclopentadienyl) zirconium dichloride, (2,7-dimesityl fluorenyl) (cyclopentadienyl) zirconium dichloride, (2,7-di(alphamethyl vinyl)fluorenyl) (cyclopentadienyl) zirconium dichloride, (1-methyl fluorenyl) (cyclopentadienyl) zirconium dichloride, (2-t-butyl fluorenyl) (cyclopentadienyl) zirconium dichloride, (2-ethyl fluorenyl) (cyclopentadienyl) zirconium dichloride, (4-methyl fluorenyl) (cyclopentadienyl) zirconium dichloride, (fluorenyl) (pentamethylcyclopentadienyl) zirconium dichloride, (fluorenyl) (pentamethylcyclopentadienyl) hafnium dichloride, (2,7-dimethyl fluorenyl) (pentamethylcyclopentadienyl) hafnium dichloride, (2,7-dimethylfluorenyl) (pentamethylcyclopentadienyl) zirconium dichloride, (2,7-di-t-butylfluorenyl) (pentamethylcyclopentadienyl) hafnium dichloride, (2,7-di-t-butylfluorenyl) (pentamethylcyclopentadienyl) zirconium dichloride, (2,7-diethylfluorenyl) (pentamethylcyclopentadienyl) zirconium dichloride, (4,5-dimethylfluorenyl) (pentamethylcyclopentadienyl) zirconium dichloride, (7-t-butylfluorenyl) (pentamethylcyclopentadienyl) zirconium dichloride, (fluorenyl) bis(3-methylcyclopentadienyl) zirconium chloride, and (2,7 di-t-butyl fluorenyl) bis(3-methylcyclopentadienyl) zirconium chloride.

12. A metallocene according to claim 1 selected from the group consisting of:

(2,7-dimesitylfluorenyl) (cyclopentadienyl) zirconium dichloride, (4,5-dimethylfluorenyl) (cyclopentadienyl) zirconium dichloride, (2,7-dimethylfluorenyl) (cyclopentadienyl) zirconium dichloride, (2,7-di-t-butylfluorenyl) (cyclopentadienyl) zirconium dichloride, and (1-methylfluorenyl) (cyclopentadienyl) zirconium dichloride.

13. A metallocene according to claim 4 wherein n is at least one.

14. A metallocene according to claim 13 wherein each R of (FlRn) is hydrocarbyl.

15. A metallocene according to claim 14 (FlRn) has R substituents at the 2 and 7 positions.

16. A metallocene according to claim 15 wherein each R is the same and is selected from the group consisting of methyl, t-butyl, mesityl, and alpha methyl vinyl.

17. A metallocene according to claim 15 wherein each R is aromatic.

18. A metallocene according to claim 17 consisting essentially of (2,7-dimesitylfluorenyl) (cyclopentadienyl) zirconium dichloride.

19. A metallocene according to claim 15 wherein each R of (FlRn) is alkenyl.

20. A metallocene according to claim 2 wherein Cp is indenyl.

21. A metallocene according to claim 20 wherein m is 0.

22. A metallocene according to claim 21 wherein n is a number in the range of 1 to 4.

23. A metallocene according to claim 22 wherein (FlRn) is (2,7 dimethylfluorenyl).

24. A metallocene according to claim 22 wherein (FlRn) is (2,7 diethylfluorenyl).

25. A process for polymerizing an olefin comprising contacting said olefin under suitable polymerization conditions with a catalyst system comprising a fluorenyl-containing metallocene of claim 1 and a suitable cocatalyst.

26. A process according to claim 25 wherein said cocatalyst comprises an alkylaluminoxane.

27. A process according to claim 26 wherein ethylene is polymerized.

28. A process according to claim 27 wherein said metallocene is one wherein Cp is cyclopentadienyl and each Q is a halide.

29. A process according to claim 27 wherein said metallocene is selected from the group consisting of:

(fluorenyl)(cyclopentadienyl) zirconium dichloride, (2,7-dimethylfluorenyl) (cyclopentadienyl) zirconium dichloride, (2,7-diethylfluorenyl) (cyclopentadienyl) zirconium dichloride, (2,7-dimethoxyfluorenyl) (cyclopentadienyl) zirconium dichloride, (4-methyl-5-methylfluorenyl) (cyclopentadienyl) zirconium dichloride, (2,7-dimesitylfluorenyl) (cyclopentadienyl) zirconium dichloride, (2,7-di(alphamethyl vinyl) (fluorenyl) (cyclopentadienyl) zirconium dichloride, (1-methylfluorenyl) (cyclopentadienyl) zirconium dichloride, (2-t-butylfluorenyl) (cyclopentadienyl) zirconium dichloride, (2-ethylfluorenyl) (cyclopentadienyl) zirconium dichloride, (4-methylfluorenyl) (cyclopentadienyl) zirconium dichloride, (fluorenyl) (pentamethylcyclopentadienyl) zirconium dichloride, (fluorenyl) (pentamethylcyclopentadienyl) hafnium dichloride, (2,7-dimethylfluorenyl) (pentamethylcyclopentadienyl) hafmium dichloride, (2,7-dimethylfluorenyl) (pentamethylcyclopentadienyl) zirconium dichloride, (2,7-di-t-butylfluorenyl) (pentamethylcyclopentadienyl) hafnium dichloride, (2,7-di-t-butylfluorenyl) (pentamethylcyclopentadienyl) zirconium dichloride, (2,7-diethylfluorenyl) (pentamethylcyclopentadienyl) zirconium dichloride, (4,5-dimethylfluorenyl) (pentamethylcyclopentadienyl) zirconium dichloride, (7-t-butylfluorenyl) (pentamethylcyclopentadienyl) zirconium dichloride, (fluorenyl) bis(3-methylcyclopentadienyl) zirconium chloride, and (2,7-di-t-butylfluorenyl) bis(3-methylcyclopentadienyl) zirconium chloride.

30. A process according to claim 27 wherein said metallocene is selected from the group consisting of (2,7-dimesitylfluorenyl) (cyclopentadienyl) zirconium dichloride, (4,5-dimethylfluorenyl) (cyclopentadienyl) zirconium dichloride, (2,7-dimethylfluorenyl) (cyclopentadienyl) zirconium dichloride, (2,7-di-t-butylfluorenyl) (cyclopentadienyl) zirconium dichloride, bis (methylcyclopentadienyl) (fluorenyl) zirconium chloride, (2,7-dimethylfluorenyl) (pentamethylcyclopentadienyl) zirconium dichloride, and (1-methylfluorenyl) (cyclopentadienyl) zirconium dichloride.

31. A process according to claim 30 wherein ethylene homopolymer is produces.

32. A process according to claim 30 wherein ethylene is polymerized in the presence of another alpha olefin having 4 to 8 carbon atoms.

33. A process according to claim 26 wherein propylene is polymerized.

34. A process according to claim 33 wherein propylene homopolymer is produced.

35. A process according to claim 34 wherein said metallocene is selected from the groups consisting of (2,7-dimesitylfluorenyl) (cyclopentadienyl) zirconium dichloride, (4,5-dimethylfluorenyl) (cyclopentadienyl) zirconium dichloride, (2,7-dimethylfluorenyl) (cyclopentadienyl) zirconium dichloride, (2,7-di-t-butylfluorenyl) (cyclopentadienyl) zirconium dichloride, bis (methylcyclopentadienyl) (fluorenyl) zirconium chloride, (2,7-dimethylfluorenyl) (pentamethylcyclopentadienyl) zirconium dichloride, and (1-methylfluorenyl) (cyclopentadienyl) zirconium dichloride. A process according to claim 27 wherein Cp is indenyl.

36. A process according to claim 27 wherein Cp is indenyl.

37. A process according to claim 36 wherein m is 0.

38. A process according to claim 37 wherein n is a number in the range of 0 to 4.

39. A process according to claim 38 wherein n is 0.

40. A process according to claim 38 wherein (FlRn) is (2,7 dimethyl fluorenyl).

41. A process according to claim 38 wherein (FlRn) is (2,7 diethylfluorenyl).

42. An unbridged metallocene of the formula $(FlR_n)(CpR_m)_2MeQ$ wherein Fl is a fluorenyl radical, Cp is a cyclopentadienyl, indenyl, or tetrahydroindenyl radical, each R is the same or different and is an organo radical having 1 to 20 carbon atoms, Me is metal selected from the group consisting of IVB, VB, and VIB metals of the Periodic Table, each Q is the same or different and is selected from the group consisting of hydrocarbyl or hydrocarbyloxy radicals having 1 to 20 carbon atoms, and halogens, n is a number in the range of 0 to 8, m is a number in the range of 0 to 7, further characterized by the fact that the Fl has no R in the 9 position.

43. A metallocene according to claim 42 named (fluorenyl) bis(methylcyclopentadienyl) zirconium chloride.

44. A metallocene according to claim 42 wherein $(FlR_n)$ is unsubstituted fluorenyl, $(CpR_m)$ is unsubstituted cyclopentadienyl, Q is unsubstituted fluorenyl, and Me is selected from the group consisting of Zr and Hf.

45. A metallocene according to claim 42 named (2,7-dimethylfluorenyl) bis(3-methylcyclopentadienyl) zirconium chloride.

46. A process for polymerizing an olefin comprising contacting said olefin under suitable polymerization conditions with a catalyst system comprising a fluorenyl-containing metallocene of claim 42 and a suitable cocatalyst.

47. A process according to claim 46 wherein said cocatalyst comprises alkylaluminoxane and ethylene is polymerized.

48. A process according to claim 47 wherein the metallocene bis(cyclopentadienyl) bis(fluorenyl) zirconium is employed.

* * * * *

UNITED STATES PATENT AND TRADEMARK OFFICE
CERTIFICATE OF CORRECTION

PATENT NO. : 5,627,247

DATED : May 6, 1997

INVENTOR(S) : Helmut G. Alt et al

It is certified that error appears in the above-identified patent and that said Letters Patent is hereby corrected as shown below:

Column 12, line 27, after "dichloride," please insert ---(2,7-di-t-butyl fluorenyl) (cyclopentadienyl) zirconium dichloride---.

Column 13, line 20, after "dichloride." please delete "A process according to claim 27 wherein Cp is indenyl".

Signed and Sealed this

Twenty-second Day of July, 1997

Attest:

BRUCE LEHMAN

*Attesting Officer*    *Commissioner of Patents and Trademarks*